United States Patent
Aelen et al.

(10) Patent No.: US 12,042,584 B2
(45) Date of Patent: Jul. 23, 2024

(54) BREAST PUMP ARRANGEMENT

(71) Applicant: KONINKLIJKE PHILIPS N.V., Eindhoven (NL)

(72) Inventors: Paul Aelen, Eindhoven (NL); Aafje Gijsbertha Koster, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1000 days.

(21) Appl. No.: 16/970,666

(22) PCT Filed: Feb. 25, 2019

(86) PCT No.: PCT/EP2019/054503
§ 371 (c)(1),
(2) Date: Aug. 18, 2020

(87) PCT Pub. No.: WO2019/166348
PCT Pub. Date: Sep. 6, 2019

(65) Prior Publication Data
US 2020/0384170 A1    Dec. 10, 2020

(30) Foreign Application Priority Data
Feb. 28, 2018 (EP) .................................... 18159065

(51) Int. Cl.
*A61M 1/06* (2006.01)

(52) U.S. Cl.
CPC ............ *A61M 1/06* (2013.01); *A61M 1/0693* (2021.05); *A61M 1/0697* (2021.05);
(Continued)

(58) Field of Classification Search
CPC .................. A61M 1/06; A61M 1/0693; A61M 2205/3334; A61M 2205/3389
See application file for complete search history.

(56) References Cited

U.S. PATENT DOCUMENTS 4,346,596 A * 8/1982 Diamant ................. G01F 15/08
                                                                            73/215
4,476,719 A * 10/1984 Millar ...................... G01F 1/00
                                                                            73/215

(Continued)

FOREIGN PATENT DOCUMENTS

| JP | 2008284270 | 11/2008 |
| WO | 2012/114217 | 8/2012 |
| WO | 2017/108555 | 6/2017 |

OTHER PUBLICATIONS

International Search Report and Written Opinion Dated May 22, 2019 for International Application Nymber PCT/EP2019/054503 Filed Feb. 25, 2019.

(Continued)

*Primary Examiner* — Quynh-Nhu H. Vu

(57) ABSTRACT

A breast pump arrangement having an expression kit with a milk flow sensor (200) is provided. The milk flow sensor (200) comprises a container (240) with a first end with a first opening (242) and a second end with a second opening (243). The second opening (243) allows an outflow of milk with a predefined outflow characteristics out of the container (241). The first opening (242) is larger than the second opening (243). A milk amount sensor (250) is provided to measure a height or volume of milk in the container. A calculating unit (260, 240) calculates a milk flow based on the height or volume measurements and the predefined outflow characteristic of the second opening (243).

10 Claims, 6 Drawing Sheets

(52) U.S. Cl.
CPC ............... *A61M 2205/3306* (2013.01); *A61M 2205/3317* (2013.01); *A61M 2205/3334* (2013.01); *A61M 2205/3389* (2013.01); *A61M 2205/3576* (2013.01)

(56) References Cited

U.S. PATENT DOCUMENTS

| | | | | |
|---|---|---|---|---|
| 5,263,370 | A * | 11/1993 | Murata | G01F 3/38 |
| | | | | 73/304 R |
| 6,741,942 | B2 * | 5/2004 | Kapitulskiy | G01F 3/38 |
| | | | | 702/45 |
| 6,796,188 | B2 * | 9/2004 | Bond | G01F 1/007 |
| | | | | 73/861.04 |
| 9,185,875 | B2 * | 11/2015 | De Groot | A01J 5/01 |
| 10,052,418 | B2 * | 8/2018 | Simmons | A61M 1/06 |
| 11,452,277 | B2 * | 9/2022 | Mostert | G01F 3/36 |
| 2008/0079488 | A1 | 4/2008 | Albrecht | |
| 2009/0254029 | A1 | 10/2009 | Tashiro | |
| 2012/0309333 | A1 | 12/2012 | Nambu | |
| 2016/0082166 | A1 | 3/2016 | Guthrie | |
| 2016/0296681 | A1 * | 10/2016 | Gaskin | A61M 1/06 |
| 2017/0021068 | A1 | 1/2017 | Gaskin | |
| 2017/0115145 | A1 * | 4/2017 | van Dijk | A01J 5/01 |
| 2017/0220753 | A1 | 8/2017 | Guthrie | |

OTHER PUBLICATIONS

Prime, et al: "Comparison of the Patterns of Milk Ejection During Repeated Breast Expression Sessions in Women", Breastfeeding Medicine, 6(4), 183-190, Jul. 19, 2011.

* cited by examiner

BREAST PUMP ARRANGEMENT

CROSS REFERENCE TO RELATED APPLICATIONS

This application is the U.S. National Phase application under 35 U.S.C. § 371 of International Application No. PCT/EP2019/054503 filed Feb. 25, 2019, published as WO 2019/166348 on Sep. 6, 2019, which claims the benefit of European Patent Application Number 18159065.4 filed Feb. 28, 2018. These applications are hereby incorporated by reference herein.

FIELD OF THE INVENTION

The present invention relates to a breast pump arrangement and a method of controlling a breast pump arrangement.

BACKGROUND OF THE INVENTION

A breast pump arrangement is used by women in order to express milk from their breasts. The amount of milk which a user can extract via the breast pump arrangement can vary over time and may also depend on several other factors. In order to improve the milk output, a user typically wants to track the amount of milk that can be extracted by means of a breast pump arrangement.

US 2017/0220753 discloses a sensor network for breast pumping mothers. Sensors are provided at a neck of a milk collection container. The sensors measure a flow rate of milk dripping into the milk container. The sensors can be capacitive sensors. The sensors can also be volume sensors which measure a liquid level by means of capacitor sensors, ultrasonic sensors, microphones or optical sensors. The sensors are arranged between a breast shield and the milk collecting container. The spout is used to allow milk to pool and to fall in a controlled manner in drops into the container. These drops are detected by the sensors. Based on the measured drops falling out of the spout, milk volume information can be generated.

SUMMARY OF THE INVENTION

It is therefore an object of the invention to provide a breast pump arrangement which allows a user to track the amount of milk which has been expressed by means of the breast pump arrangement.

According to an aspect of the invention, a breast pump arrangement is provided which comprises at least one expression kit which has a milk flow sensor. The milk flow sensor comprises a container with a first and second end having a first and second opening, respectively. The first end with the first opening is configured to receive expressed milk. The first opening is larger than the second opening. The second opening is configured to allow an outflow of milk with a predefined outflow characteristic from the inside of the container. The milk flow sensor comprises a milk-amount sensor configured to measure a height or a volume of milk in the container. The milk flow sensor furthermore comprises a calculating unit configured to determine a milk flow based on the height or volume measurements from the milk-amount sensor and the predefined outflow characteristic of the second opening.

By providing a container with a predefined outflow rate like an outflow characteristics and by detecting the amount of milk inside the container, it is possible to determine the milk flow. The use of a container with a predefined outflow characteristics is advantageous as it allows the determination of a milk flow and based on this information the volume of extracted milk. When the breast pump is activated, milk is typically ejected in bursts. The ejected milk can then flow into the container from where an amount of milk, namely according to the predefined milk outflow characteristic, is flowing out of the container, e.g. into a bottle. By measuring the height or the volume of milk in the container over a time, the calculating unit can determine how much milk has flown from the container for example into a bottle collecting the milk. Because of the predefined outflow characteristic of milk from inside the container during the operation of the breast pump, an amount of milk will accumulate in the container. The predefined outflow characteristic depends on the shape of the container and in particular the shape of the second opening. If the diameter of the second opening is smaller, obviously the outflow will be reduced. The outflow characteristic may also take into account the amount of milk inside the container. The outflow characteristic will be determined by the configuration of the container and the second opening. This is a design choice during the construction of the container. Once these characteristics are known, the calculating unit can use this information in order to determine the milk flow. The milk-amount sensor measures the height or volume of this accumulated milk. The calculating unit can integrate the detected milk flow over time to calculate the milk volume.

According to an aspect of the invention, the milk flow sensor acts as a leaky integrator. The burst of milk enter the container at the first end and the milk from the container will flow out of the container at a predetermined outflow through the second opening.

According to an aspect of the invention, the volume outflow of milk out of the container is determined as follows:

$$V_{dot} = C_c * C_v * A_{aperture} * \mathrm{Sqrt}(2*9.81*h)$$

with $V_{dot}$ is the volume flow of milk,
$A_{aperture}$ is the area of the opening in the bottom,
$C_c$ is the contraction coefficient of the opening and
$C_v$ is the velocity coefficient of the milk and
h is the height of milk in the container.

According to an aspect of the invention, the container is rigid, i.e. the container does not deform. This is advantageous in order to avoid the influence of any deformation of the container on the height or volume measurements.

According to an aspect of the invention, the milk sensor can measure a height or volume of the milk based on a capacitance, resistance or optical measurement.

According to an aspect of the invention, the breast pump arrangement comprises a breast pump unit. A part of the milk sensor, namely the electronics and possibly the calculating unit, may be part of the pump unit.

According to an aspect of the invention, the milk-amount sensor is a capacitance sensor which comprises two metal plates along the walls of the container. Preferably, the metal plates are embedded in a non-conducting material. As the container is stiff or rigid, the metal plates will not move, thereby not decreasing the accuracy of the measurements. The capacitance of the two plates will change if milk is accumulated inside the container and thus between the two plates. These capacitance changes can be detected and the milk flow can be determined.

According to an aspect of the invention, the amount of milk inside the container can be determined by measuring the electrical resistance between two plates. The two electrically conductive plates may be partially embedded with a non-conducting material. However, at least part of the two electrically conductive plates should not be covered by the non-conducting material in order to allow an electrical connection such that a resistance measurement can be performed.

According to a further aspect of the invention, the milk sensor is embodied as an optical sensor having a plurality of light emitting units and a plurality of detector units along the wall of the container. The detector units will detect the amount of light emitted by the light units. If milk has accumulated inside the container, this will have an influence on the amount of light which is detected by the detector units. Thus, the height of the accumulated milk can be determined by means of the optical milk sensor.

Other aspects of the invention are described in the dependent claims. Further advantages and embodiments of the invention will now be elucidated with reference to the drawings.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
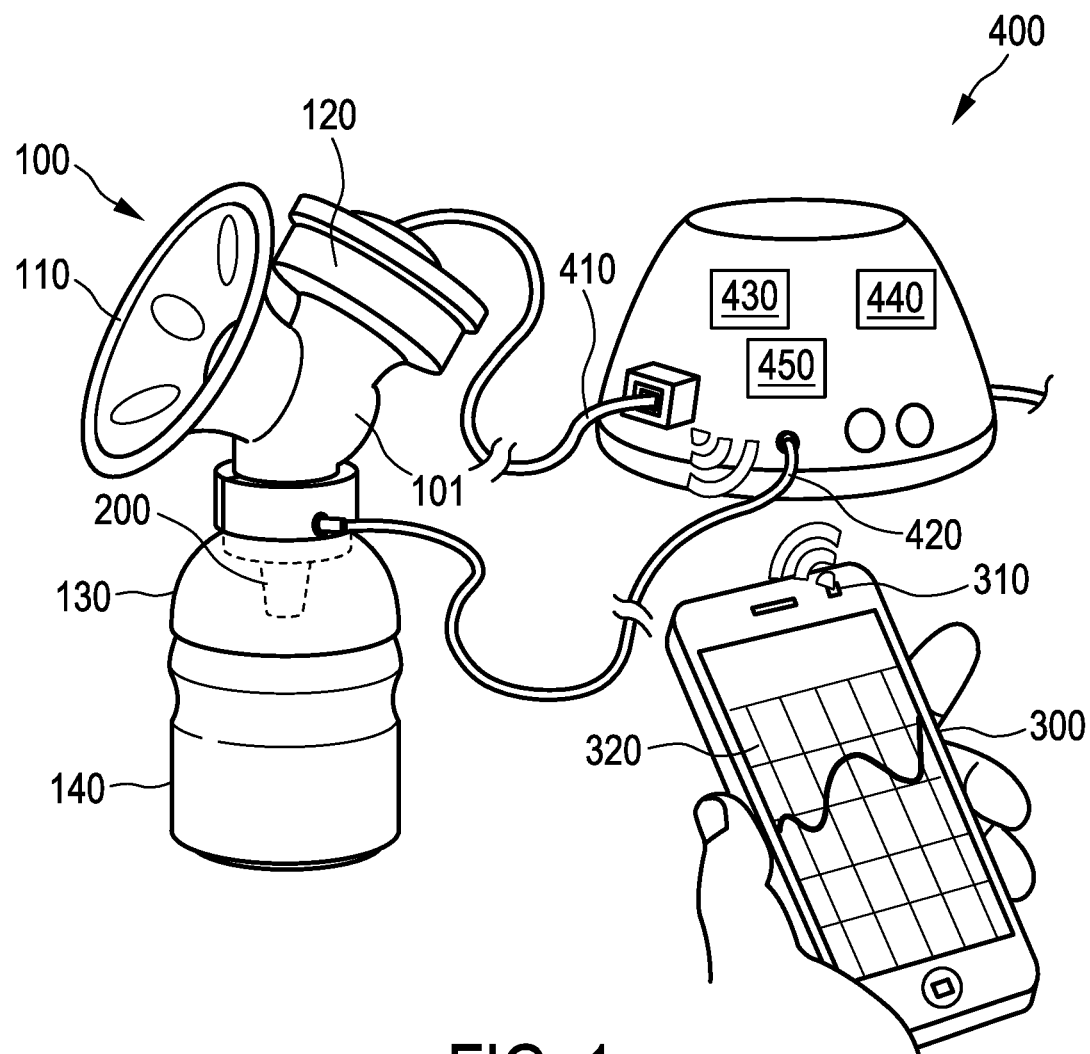
FIG. 1 shows a schematic representation of a breast pump arrangement according to an aspect of invention.

FIG. 1 shows a schematic representation of a breast pump arrangement according to an aspect of invention. The breast pump arrangement comprises an expression kit 100 and a pump unit 400. The expression kit 100 comprises a first port 101 which can receive a suction hood 110 and a second port 120 and a third port 130 for a bottle 140. Furthermore, the expression kit 100 comprises a milk flow sensor 200 which can be optionally arranged at the third port 130. A vacuum conduit 410 is coupled between the pump unit 400 and the second port 120. An electric line 420 can be coupled between the pump 400 and the milk flow sensor 200. The pump unit 400 can comprise a vacuum pump 430 and a control unit 440 for controlling the operation of the pump unit 400 in particular to control the pressure to generate a vacuum in the suction hood 110 and part of the expression kit 100 via the vacuum conduit 410 when a breast is placed into the suction hood 110. The control unit 440 can be coupled via the electrical line 420 to the milk flow sensor 200. The pump unit 400 may also comprise a wireless transceiver 450.

A smart device 300 having a wireless transceiver 310 as well as a display 320 may communicate with the pump unit 400 via the transceiver 450. The control unit 440 can forward milk flow information to the electronic device 300 which can display this information on the display 320.

Figure 2:
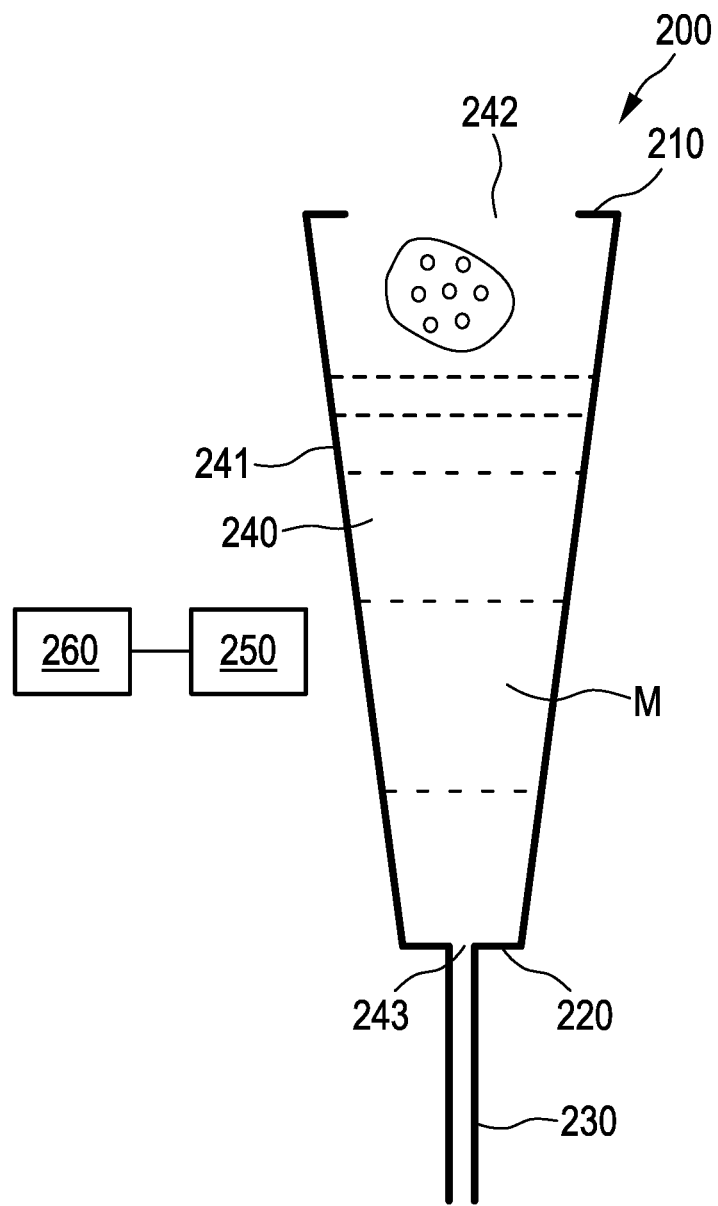
FIG. 2 shows a schematic cross section of a milk flow sensor according to an aspect of the invention.

FIG. 2 shows a schematic cross section of a milk flow sensor according to an aspect of the invention. The milk flow sensor 200 comprises a container 240 which has a first end 210 and a second end 220. At the first end 210, a first opening 242 and at the second end 220 a second opening 243 is provided. The second opening 243 is embodied to allow a predetermined outflow of milk or an outflow with a predefined outflow characteristic. The wall 241 of the container can be e.g. funnel shaped. Accordingly, the width of the first opening 242 is greater than the width of the second opening 243. The outflow characteristics of the container are determined by the configuration and shape of the second opening. Accordingly, the outflow characteristics are predefined, namely during the construction or design of the container. The flow rate may thus increase with an increasing milk volume in the container. A milk amount sensor 250 is used to measure a height or volume of the milk in the container 240. The milk-amount sensor 250 can be coupled to a calculating unit 260 which determines a milk flow based on the height and volume measurements of the milk-amount sensor 250. The calculating unit 260 can be part of the milk flow sensor 200 or the control unit in the pump unit 400 can perform the calculation. The calculating unit 260 determines a volume outflow of milk out of the container based on the following equation:

$$V_{dot} = C_c * C_v * A_{aperture} * \text{Sqrt}(2*9.81*h)$$

with $V_{dot}$, is the volume flow of milk,
$A_{aperture}$ is the area of the opening in the bottom,
$C_c$ is the contraction coefficient of the opening and
$C_v$ is the velocity coefficient of the milk and
h is the height of milk in the container.

Figure 3:
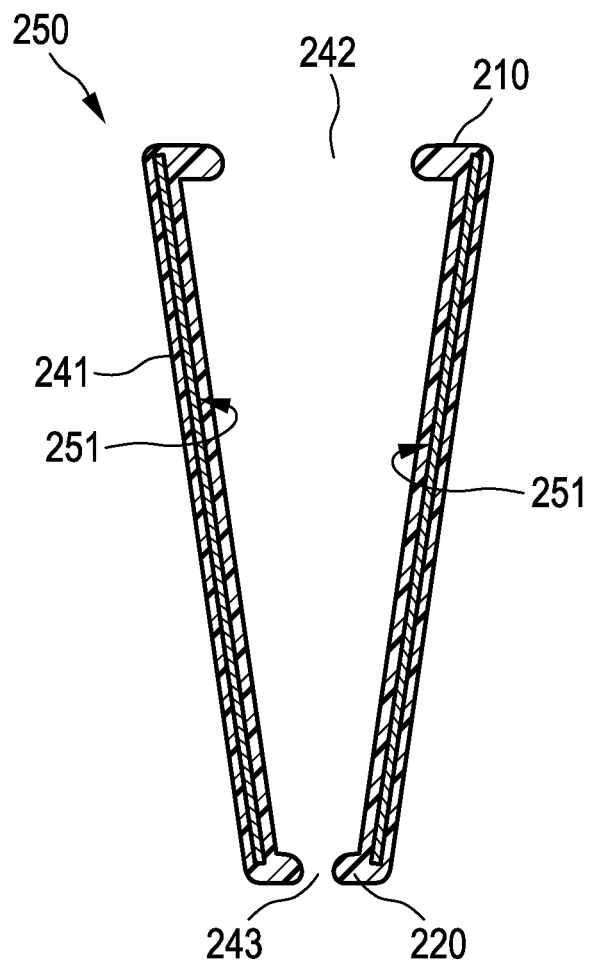
FIG. 3 shows a schematic cross section of a milk flow sensor according to an aspect of the invention.

FIG. 3 shows a schematic cross section of a milk flow sensor according to an aspect of the invention. In FIG. 3, a specific implementation of the milk-amount sensor 250 as capacitance sensor is depicted. The milk-amount sensor 250 comprises two metal plates 251 in the wall 241 of the container. The two metal plates 251 act as the two plates of a capacitor to allow a capacitance measurement. The measured capacitance will depend on the amount of milk inside the container. Thus, any changes in the amount of milk in the container 240 will result in changes of the capacitance.

The structure of the container with the first and second ends and first and second openings substantially correspond to the container of FIG. 2.

Figure 4:
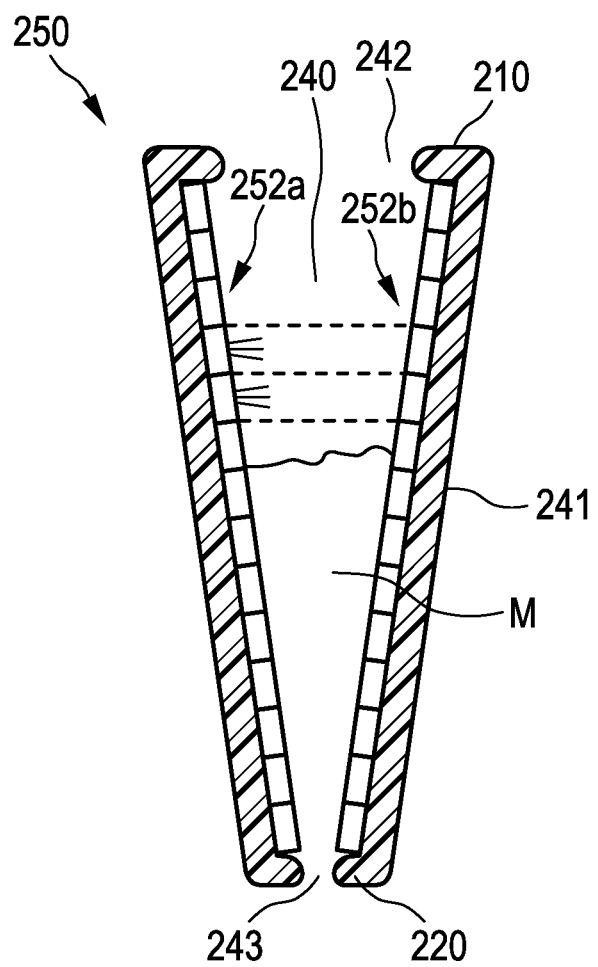
FIG. 4 shows a schematic cross section of a milk flow sensor according to an aspect of the invention.

FIG. 4 shows a schematic cross section of a milk flow sensor according to an aspect of the invention. Inside the container 240, the milk-amount sensor 250 is embodied as an optical sensor having a plurality of light units 252a for emitting light and a plurality of detector units 252b for detecting the emitted light. The detected light will depend on the amount of milk inside the container. The arrangement of the container according to FIG. 4 substantially corresponds to the arrangement of the container according to FIG. 2.

According to a further aspect of the invention, the milk amount sensor can be embodied as a resistive milk flow sensor which comprises a first and second electrically conductive plate 251. In particular, the electrical resistance between the two plates at the wall 241 of the container is detected. Accordingly, the plates are at least partially in direct contact with the milk inside the container 240. Optionally, the resistive milk amount sensor may be configured analog to the optical sensor, namely with a number of plates along the wall 241.

The optical milk sensor according to FIG. 4 determines a height of the milk volume and thereby can determine the volume of the milk.

Figure 5:
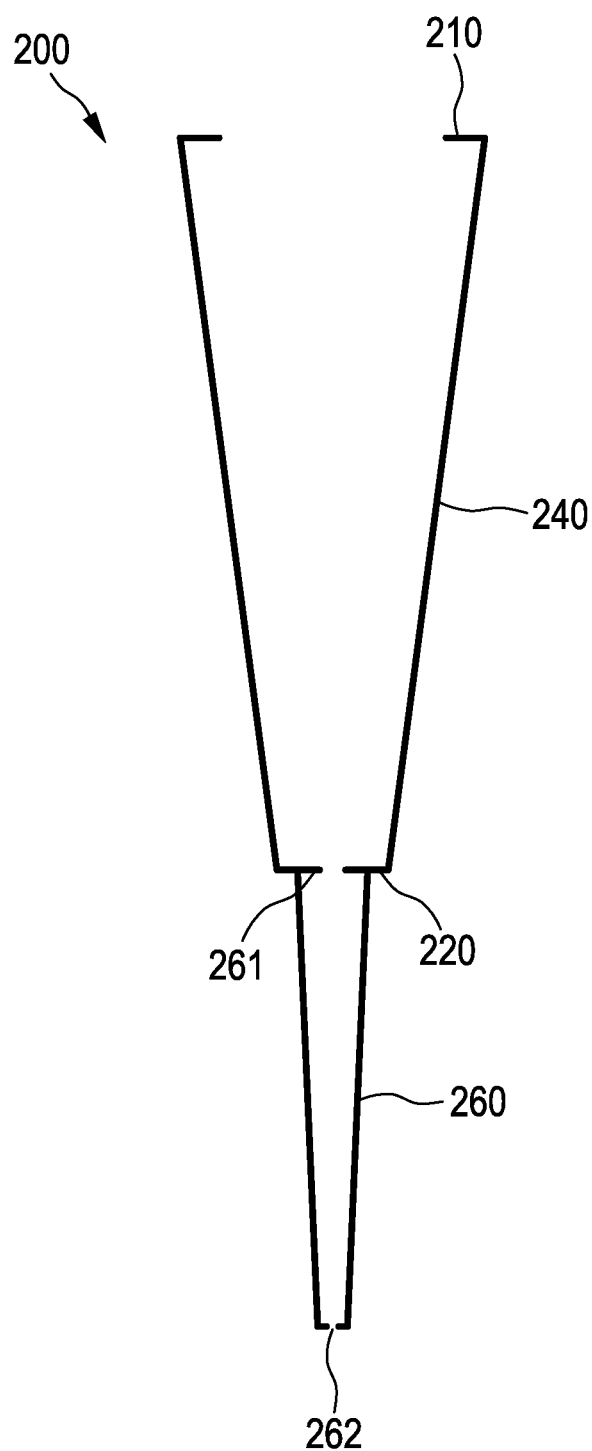
FIG. 5 shows a schematic cross section of a milk flow sensor according to an aspect of the invention.

FIG. 5 shows a schematic cross section of a milk flow sensor according to an aspect of the invention. The container according to this aspect of the invention comprises an upper part which substantially corresponds to the containers according to FIG. 2, 3 or 4 as well as a lower part 260 which is coupled to the second end 220 of the container 240. The lower part 260 of the container can be added to improve a measurement resolution. In particular, the lower part 260 is coupled to the second end of the container 240 and comprises a higher height to width ratio.

The multiple funnel shaped container elements of FIG. 5 can be stacked on top of each other in order to have an improved measurement resolution even at lower milk flows.

According to an aspect of the invention, the second opening 243 allows a pre-determined outflow. This predetermined outflow is determined by the size and shape of the opening 243.

The milk sensor according to FIG. 3 measures the volume of the milk capacitively.

According to an aspect of the invention, the container 240 is of a non-deformable material. In particular, the construction of the container 240 is stiff or rigid in order to avoid any deformation which would reduce the accuracy of the flow sensor.

According to an aspect of the invention, the output restriction of the milk flow is shaped such that the milk inside the container empties within a complete vacuum cycle.

According to a further aspect of the invention, the height of the container can be big compared to the width. In other words, the height/width ratio is big. This is advantageous as the angle dependence of this configuration is small.

Figure 6:
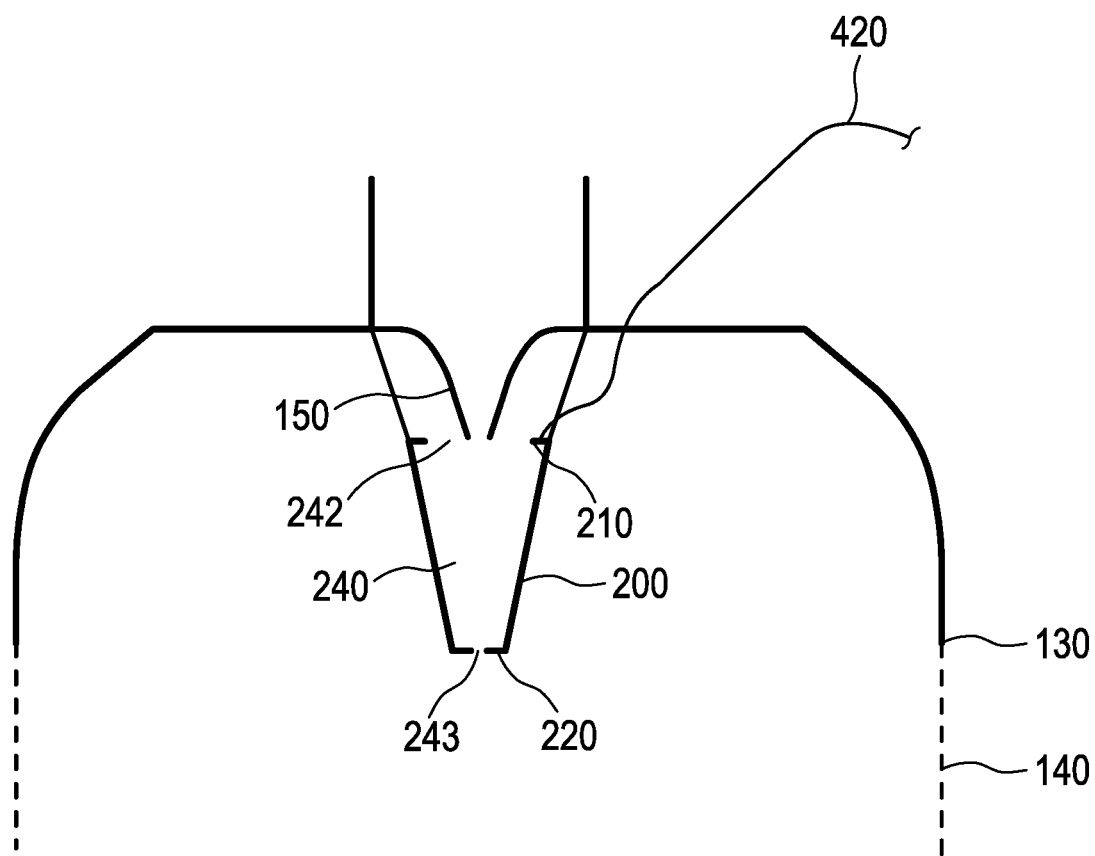
FIG. 6 shows a schematic cross section of a milk flow sensor according to a further aspect of the invention.

FIG. 6 shows a schematic cross section of a milk flow sensor according to a further aspect of the invention. The container 240 can be arranged under a one way valve 150 of the expression kit. The one-way valve is provided as a vacuum pressure build up needs to be generated followed by emptying in the bottle. The container 240 can thus be arranged below the valve 150.

As described with reference to FIG. 1, the milk flow or the milk volume can be wirelessly transmitted by the transmitter 450 to the electronic device 300 and can be displayed on its display 320. Thus, the user can determine the optimal settings for the extraction of milk.

As the pump 400 receives the milk flow information from the milk flow sensor 200, the operation of the pump can be adjusted based on this information. In particular, the vacuum cycle can be adapted in order to improve the milk output. The current milk output information can be compared to older milk output information in order to determine whether the milk output has improved or has decreased. Furthermore, a profile can be created with an optimal milk output. The pump 400 can adapt the cycle time and the maximum vacuum pressure level in order to improve the milk output.

If the current milk output is too low, the user may receive information to trigger the stimulating settings to stimulate another milk ejection reflex and to thereby improve the milk output.

According to an aspect of the invention, the breast pump settings are automatically switched to the stimulation settings as soon as the milk flow is below a predetermined level.

If the flow drops below a predetermined level for a predetermined amount of time, the user may be advised to stop expressing milk.

Other variations of the disclosed embodiment can be understood and effected by those skilled in the art in practicing the claimed invention from a study of the drawings, the disclosure and the appended claims.

In the claims, the word "comprising" does not exclude other elements or steps and in the indefinite article "a" or "an" does not exclude a plurality.

A single unit or device may fulfil the functions of several items recited in the claims. The mere fact that certain measures are recited in mutual different dependent claims does not indicate that a combination of these measurements cannot be used to advantage. A computer program may be stored/distributed on a suitable medium such as an optical storage medium or a solid state medium, supplied together with or as a part of other hardware, but may also be distributed in other forms such as via the internet or other wired or wireless telecommunication systems.

Any reference signs in the claims should not be construed as limiting the scope.

The invention claimed is:

1. A breast pump arrangement, comprising at least one expression kit having a milk flow sensor, wherein the milk flow sensor comprises:
    a container with a first end with a first opening and a second end with a second opening, wherein the first end of the container is configured to receive expressed milk (M), wherein the second opening is configured to allow an outflow of milk (M) with a predefined outflow characteristic from inside the container, wherein the first opening is larger than the second opening,
    a milk-amount sensor configured to measure a height or volume of milk (M) in the container, and
    a calculating unit configured to calculate a milk flow based on the height or volume measurements of the milk-amount sensor and the predefined outflow characteristic of the second opening.

2. The breast pump arrangement according to claim 1, wherein the container is rigid.

3. The breast pump arrangement according to claim 1, wherein the milk-amount sensor is embodied as a capacitive sensor.

4. The breast pump arrangement according to claim 1, wherein the milk-amount sensor is embodied as a resistive sensor.

5. The breast pump arrangement according to claim 1, wherein the milk-amount sensor is embodied as an optical sensor.

6. The breast pump arrangement according claim 1, further comprising a pump unit having a vacuum pump, said pump unit is coupled via a vacuum conduit to the expression kit in order to create a vacuum in the expression kit to allow an expression of milk (M), wherein the pump unit further comprises a control unit which is adapted to control an operation of the vacuum pump to set vacuum settings at the expression kit depending a determined milk flow.

7. The breast pump arrangement according to claim 6, wherein the control unit is adapted to change the operation of the vacuum pump if a milk flow threshold is exceeded or if the milk flow is below the milk flow threshold.

8. The breast pump arrangement according to claim 6, further comprising an electrical line coupling the milk flow sensor with the pump unit.

9. The breast pump arrangement according to claim 7, wherein the pump unit further comprises a wireless transceiver configured for wirelessly transmitting the determined milk flow.

10. The breast pump arrangement according to claim 1, wherein the calculating unit calculates the milk flow (Vdot) by using following equation:

$$\text{Vdot} = Cc * Cv * \text{Aaperture} * \text{Sqrt}(2*9.81*h)$$

Wherein Vdot is a volume flow of milk (M),
wherein Aaperture is an area of the second opening,
wherein Cc is a contraction coefficient of the second opening and
Cv is a velocity coefficient of the milk (M),
wherein h is a height of the milk (M) inside the container.

* * * * *